US00PP08265P

United States Patent [19]

Klemm

[11] Patent Number: Plant 8,265

[45] Date of Patent: Jun. 15, 1993

[54] GERANIUM PLANT NAMED KLEMIR

[75] Inventor: Siegfried Klemm, Stuttgart, Fed. Rep. of Germany

[73] Assignee: Klemm & Sohn, Fed. Rep. of Germany

[21] Appl. No.: 804,051

[22] Filed: Dec. 9, 1991

[51] Int. Cl.[5] ..... A01H 5/00
[52] U.S. Cl. ..... Plt./87.12
[58] Field of Search ..... Plt./87.12

*Primary Examiner*—James R. Feyrer
*Attorney, Agent, or Firm*—Tilton, Fallon, Lungmus & Chestnut

[57] ABSTRACT

A new and distinctive Geranium variety particularly distinguished by profuse production of mandarin red colored flowers which form medium size round clusters of 40 to 50 florets. The cluster stalk stands upright holding the flower clusters above the dark green zonated leaves in a bush of about 35 cm. in height. 'Klemir' differs from other orange varieties in that it has small and very round clusters with many long lasting flowers in a deep salmon orange color. These eye catching clusters stand on rather long and strong, green stalks on a plant that grows compactly bushy and less than medium height. Previous orange flowered zonal geraniums grew higher. Additionally another distinction is the solid dark green leaves with their dark zonation and their good resistance against cold, heat and rainy weather.

1 Drawing Sheet

BACKGROUND OF THE NEW PLANT

My new Geranium cultivar originated as a hybrid seedling produced by my crossing the variety "PAC Palais" with the pollen of our own seedling "D78" in 1987 in my nursery at Stuttgart, Germany. This seedling bloomed for the first time in 1987 and because of its outstanding growth habit, its profuse blooms, and the flower color, the seedling was selected for propagation which was done by me and under my direction at Stuttgart by means of cuttings. Successive generations of this plant have shown that its novel and distinguishing characteristics are fixed and hold true from generation to generation.

DESCRIPTION OF THE DRAWING

This new Geranium cultivar is illustrated by the accompanying photographic drawing, which shows a fully developed plant with several clusters of flowers and buds which illustrate their form and their mandarin red coloring; the color rendition being as nearly true to that herein specified as is reasonably possible to obtain by conventional photographic procedures.

DESCRIPTION OF THE PLANT

The following is a detailed description of a new Geranium variety as observed of plants both grown in greenhouse and outdoors at Stuttgart with color designation according to The R.H.S. Colour Chart published by The Royal Horticultural Society of London, England.

THE PLANT

Origin: Seedling.
Parentage:
*Seed parent.*—'PAC Palais' (unpatented). Color: Salmon with a small white border. Precocity: early. Growth habit: low to medium high. The color of the flower is distinctive and the clusters are rather large. The continuity of flowering is good during the whole season. The leaves can withstand heat without changing color or getting botrytis.

*Pollen parent.*—'D 88' (unpatented). D88 is an unpatented seedling bred in 1985. Flower color: orange with a very white and visible border. Precocity: early to medium. Growth habit: too big and too high for commercial use. The leaves are large with a nice zonation. In the cross 'Klemir' deep salmon orange color was obtained with small clusters than the parent. The growth habit of 'Klemir' is more like 'Palais' but the cluster stems are longer so that the whole shape of the plant is different than 'Palais'.

Classification:
*Botanic.*—*Pellargonium peltatum.*
*Commercial.*—Geranium.
Form: Bush.
Height: About 35 cm. without flower clusters.
Growing rate: Approximately 75 days. Internode length varies from between 0.5 to 1.5 cm. Pinching is not required.
Branching character: Medium.
*Cluster stems.*—About 15-20 cm. long.
Growth habit: Upright and vigorous.
*Strength.*—Very good.
Foliage:
*Quantity.*—Average.
*Shape of leaf.*—Generally uniform. Leaf margin: Bicrenate.
*Leaf coloration.*—Upper side RHS 137A-147A. Bottom surface: RHS 147B. Coloration of zonation: RHS 139A-147A.
*Size.*—About 7-8 cm. wide.
*Texture.*—Smooth.
*Color.*—Upper side — Green with brown zonation. Under side —A shade lighter.

THE BUD

Size: Medium.
*Diameter.*—About 9 mm.
*Length.*—About 15 mm.
Shape: Ovoid and pointed.
Opening rate: Medium.
Color of petals:

*When sepals first open.*—White to light red.

Sepals:

*Number.*—5.

*Shape.*—Small and pointed.

*Character.*—Sepals are not hooded or branched. The sepals stand up when the flower opens.

*Color.*—Inside — Light green. Outside — Medium green.

INFLORESCENCE

Blooming habit: Medium and continuous from early spring to fall.

Size of cluster:

*Diameter.*—In average about 8 cm.

*Depth.*—In average about 6.5 mm.

*Borne.*—It is not necessary to pinch withered umbels. Upriht on strong green stalks. This measurement is made when the cluster is fully blooming.

Cluster stem:

*Length.*—About 10–12 cm.

*Color.*—Green with a little brown.

Flowers:

*Number.*—In average, between 40 and 50.

*Form.*—Flattened cup-shaped.

Petalage:

*Number.*—About 7 or 8.

*Form.*—Broad with entire margins.

*Arrangement.*—The petals are arranged around the ovaries.

*Texture.*—Soft.

Appearance.—Satiny.

Color:

*Outer petals.*—Body — 40-C. Base — 40-D. Reverse side — 41-C.

*Inside petals.*—Body — 41-B. Base — 41-C. Reverse side — 41-D.

Petaloids:

*Number.*—1 or 2.

*Size.*—Between 3 and 4 mm.

Color: 41-C.

Stems: Very strong and upright.

Discoloration: Resistant to rain, sun and heat; slight discoloration under strong direct sunlight.

Lasting quality: Approximately 30 days on the plant and 6 days as a cut flower.

Disease resistant: Botrytis resistant as observed in Stuttgart and in Italy.

THE REPRODUCTIVE ORGANS

Stamens:

*Number.*—6–75.

*Arrangement.*—They are standing in a circle on the ovaries.

Anthers:

*Size.*—About 2 mm.

*Color.*—Red.

Filaments:

*Length.*—About 6 mm.

*Color.*—White.

Pollen:

*Color.*—Orange.

Pistils: Number — 1.

*Styles.*—About 7 mm. long.

Stigmas:

*Color.*—Light red.

Characteristic of ovaries: Typical of Pelargonium.

Fruit:

*Fertility.*—The fruit is fertile.

*Shape.*—Ovoid.

*Color at maturity.*—Dark Brown.

This mandarin red Geranium is more resistant to rain, thunder and wind than the variety PAC Palais. Its growth is very strong and bushy.

I claim:

1. The new and distinctive Geranium variety, substantially as herein shown and described, characterized by its mandarin red flower clusters and its strong growth habit, being resistant against rain, sun and hot weather.

* * * * *

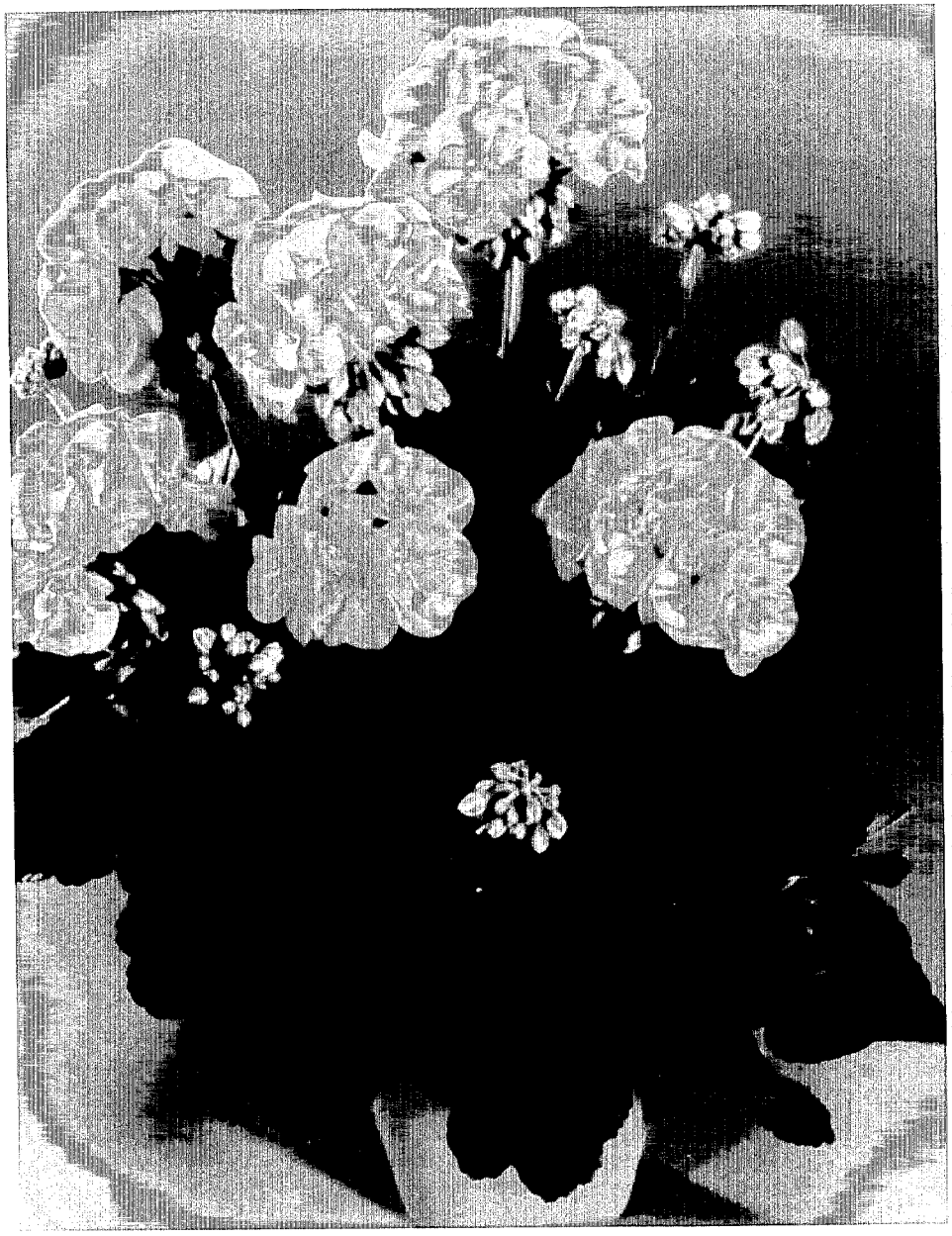

UNITED STATES PATENT AND TRADEMARK OFFICE

CERTIFICATE OF CORRECTION

PATENT NO. : PP 8,265

DATED : Jun. 15, 1993

INVENTOR(S) : Siegfried Klemm

It is certified that error appears in the above-identified patent and that said Letters Patent is hereby corrected as shown below:

Column 3, line 17, delete "Upriht" and insert --Upright--.

Signed and Sealed this

Eighteenth Day of January, 1994

*Attest:*

Bruce Lehman

BRUCE LEHMAN

*Attesting Officer*

*Commissioner of Patents and Trademarks*